United States Patent [19]

Dolling

[11] 4,237,315

[45] Dec. 2, 1980

[54] PREPARATION OF 5(HALOPHENYL)SALICYLIC ACID COMPOUNDS

[75] Inventor: Ulf H. Dolling, Westfield, N.J.

[73] Assignee: Merck & Co., Inc., Rahway, N.J.

[21] Appl. No.: 90,792

[22] Filed: Nov. 2, 1979

[51] Int. Cl.$^3$ ............................................. C07C 65/00
[52] U.S. Cl. ...................................... 562/469; 560/59
[58] Field of Search ......................... 562/469; 560/59

[56] References Cited

PUBLICATIONS

Smidt, *Chem. and Ind.* Jan. 13, 1962, pp. 54–61.
Van Helden, et al., *Recueil,* 84, pp. 1263–1273 (1965).
Stephenson, et al., *J. Chem. Soc.,* pp. 3632–3640 (1965).
Davidson, et al., *J. Chem. Soc.,* vol. 38, No. 1, pp. 76–79 (1973).
Fujiuara, et al., *Bull. Chem. Soc. Jap.,* vol. 43, No. 3, pp. 863–867 (1970).
Arzoumanidis, et al., *Chem. Tech.,* Nov. 1973, pp. 700–702.
Rudenkov, et al., *Kinetika* i Kataliz, vol. 18, No. 4, pp. 915–920 (1977).
Kokorin Zh., *Obshch Khim.,* 24, 966 (1954).

*Primary Examiner*—Paul J. Killos
*Attorney, Agent, or Firm*—Raymond M. Speer; Mario A. Monaco

[57] ABSTRACT

A method of preparing compounds of the formula:

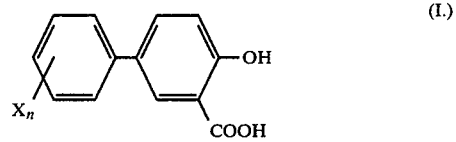

(I.)

wherein a novel palladium catalyst system is utilized comprising
  palladium together with $C_{1-2}COO^-$ ligands and halo ligands wherein the molar weight percent based on total ligand molar weight, of the $C_{1-2}COO^-$ ligand is from 30 to 60%; and
  wherein the ratio of the total molar weight of the ligands to the molar weight of palladium utilized is from 4:1 to 10:1; and
  a catalyst regeneration portion comprising from 0.1 to 8.0 parts of phosphomolybdenovanadic acid per part of palladium catalyst, and at least 20 parts of a solubilizing agent selected from ethylene carbonate, propylene carbonate, and sulfolane, per part of palladium catalyst.

7 Claims, No Drawings

PREPARATION OF 5(HALOPHENYL)SALICYLIC ACID COMPOUNDS

BACKGROUND OF THE INVENTION

1. Field of the Invention

The present invention is concerned with a novel improved method of preparing 5-(halophenyl)salicylic acid compounds in which a halobenzene compound is oxidatively coupled to an alkyl ester of salicylic acid, followed by hydrolysis of the ester.

More particularly, the present invention is concerned with preparation of 5-(2,4-difluorophenyl)salicylic acid, an important anti-inflammatory and analgesic therapeutic agent.

2. Brief Description of the Prior Art

The early use of palladium chloride catalysts in the oxidation of olefins led Van Helden et al. to a method for the oxidative coupling of aromatic compounds with palladium salts. See Smidt, Chem. and Ind., Jan. 13, 1962, pp. 54–61; and Van Helden and Verberg, Recueil, 84, pp. 1263–1273 (1965). Various modifications of this oxidative coupling method and related coupling methods have been put forward. See Stephenson et al., J. Chem. Soc., pp. 3632–3640 (1965); Davidson and Triggs, J. Chem. Soc., pp. 1331–1334 (1968); Iataaki and Yoshimoto, J. Org. Chem., Vol. 38, No. 1, pp. 76–79 (1973); Fujiuara et al., Bull. Chem. Soc. Jap., Vol. 43, No. 3, pp. 863–867 (1970); Arzoumanidis and Rauch, Chemtech, November 1973, pp. 700–702; and Rudenkov et al., Kinetika i Kataliz, Vol. 18, No. 4, pp. 915–920 (1977).

However, the methods of the prior art, when applied to the preparation of 5-(halophenyl) salicyclic acid compounds, have been found to be not only stoichiometric, i.e., not catalytic, but unselective as well, i.e., yielding the desired product in small proportions compared to other, undesired products. Thus, the methods of the prior art have been found unacceptable. The inherent problem to be overcome in the preparation of 5-(halophenyl)salicylic acid compounds by direct coupling of a halobenzene compound and an alkyl ester of salicylic acid, for example, methyl salicylate, lies in the very low reactivity of the halobenzene compound compared to the very high reactivity of the alkyl ester of salicylic acid. Thus, the predominant product of the coupling reaction is, for example, bis (methyl salicylate).

Contrary to what would be expected from the coupling methods of the prior art, the novel coupling method of the present invention provides not only a greatly improved product selectivity, but an exceptionally high catalyst turnover as well, thus affording a substantially improved method of preparing 5-(halophenyl)salicylic acid compounds.

SUMMARY OF THE INVENTION

The present invention provides a novel improved method of preparing 5-(halophenyl)salicylic acid compounds of the formula:

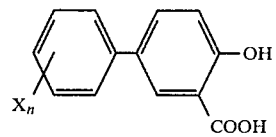

where
n is 1 or 2; and
X is chloro or fluoro.

More particularly, the present invention provides a novel improved method of preparing the compound 5-(2,4-difluorophenyl)salicylic acid, which has the following structural formula:

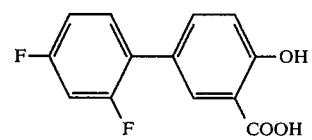

The starting materials for the novel improved method of the present invention are alkyl esters of salicylic acid of the formula:

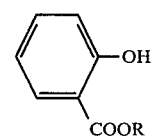

where R is $C_{1-4}$ alkyl; and halobenzene compounds of the formula:

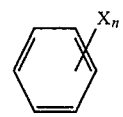

where X and n are as described above.

Where, in accordance with the preferred aspect of the present invention, the compound prepared is 5-(2,4-difluorophenyl)salicylic acid, the starting materials are methyl salicylate and m-difluorobenzene.

The novel improved method of the present invention is a two step method in which in the first step the starting materials are oxidatively coupled by means of a palladium catalyst system which affords high turnover and good selectivity. In the second step, the alkyl ester product is hydrolyzed to give the final product of Formula I.

The unique palladium catalyst system utilized in the novel improved method of the present invention affords, as indicated, good selectivity and high turnover. Together, these characteristics result in a method of dramatically improved efficiency and economics.

Selectivity refers to the ability of the catalyst system to produce the desired end product in as high a proportion as possible compared to production of other, undesired end products. In the preparation of 5-(halophenyl)salicylic acid compounds, this is an essential characteristic of the catalyst system since, as already described above, the 5-(halophenyl)salicylic acid compound is ordinarily produced in only minor proportions, while the bis(salicylic acid alkyl ester) is the predominant product, together with other undesired final products.

Turnover refers to the number of times that a catalyst system is able to convert the reactants to final products before becoming inactivated. As already described above, it has been found that the palladium catalyst systems of the prior art, when applied to the preparation of 5-(halophenyl)salicylic acid compounds as in the method of the present invention, provide only one turnover. By contrast, the method of the present invention is able to provide upwards of 200 turnovers before eventual inactivation.

It will be appreciated that the efficiency and economics of the method of the present invention are improved when either or both the selectivity and the turnover of the catalyst system are increased. In fact, the total moles of the desired final product produced per mole of catalyst, which is an expression of the overall efficiency of the catalyst system, is the product of the selectivity multiplied by the number of turnovers.

In accordance with the procedures of the novel improved method of the present invention, the catalyst portion of the palladium catalyst system comprises palladium, Pd++, together with $C_{1-2}COO^-$, i.e. acetate or propionate, preferably acetate ligands, and halo ligands selected from $Br^-$, $Cl^-$, and $F^-$, preferably chloro ligands.

It is believed that the selectivity of the catalyst is improved by achieving the proper electrophilicity of the catalyst through obtaining a proper ratio of the ligands. It has been found that the molar weight percent of the $C_{1-2}COO^-$ ligand must be from 30 to 60% of the total ligand molar weight in order to provide the desired selectivity. The molar weight percent of the acetate ligand, for example, where the other ligand is chloro, is obtained from the following formula:

$$\frac{\text{moles } CH_3COO^-}{\text{moles } CH_3COO^- + \text{moles } Cl^-} \times 100$$

The molar weight percent of the halo ligand is 100% minus the $C_{1-2}COO^-$ ligand molar weight percent, and will thus be from 40 to 70%. Preferably, the molar weight ratio of the $C_{1-2}COO^-$ and halo ligands is 1:1.

The $C_{1-2}COO^-$ ligand is most efficiently provided by utilizing palladium acetate, $Pd(CH_3COO)_2$, or palladium propionate in the system. Alkali metal acetate or propionate, preferably sodium acetate, $CH_3COONa$, is then used to provide additional amounts of $C_{1-2}COO^-$ ligand. The halo, preferably chloro ligand is provided by utilizing the appropriate halo salt of lithium, sodium, or tetra (alkyl) ammonium, preferably sodium. Thus, it is preferred to use sodium chloride, NaCl, to provide the second ligand. Conversely, however, it is also possible to use palladium chloride, $Pd(Cl)_2$, and sodium acetate to provide the necessary ligands. Thus, the proportional balance of the ligands, rather than their original source, is important.

By employing a proper balance of ligands as described above, it has been possible to increase the selectivity of the catalyst system from about 15% following the teachings of the prior art, to about 20%.

The molar weight proportions of the $C_{1-2}COO^-$ and halo ligands has been described above. It is also essential, however, that the proper molar weight ratio of ligands to palladium be utilized. Thus, the ratio of the total molar weight amount of the ligands, i.e. the sum of $C_{1-2}COO^-$ and halo, to the molar weight amount of palladium utilized, should be from 4:1 to 10:1, and is preferably near 4:1. Thus, where the ligands are acetate and chloro, the overall preferred proportions of palladium: acetate: chloro are 1:2:2.

The amount of palladium catalyst employed, preferably as the acetate, will be from 0.1 to 4.0 parts for every 500 parts on a molar basis of halobenzene compound starting material utilized. However, as is well understood, there is nothing critical in the use of larger or smaller amounts of catalyst, and the choice of amount will be one dictated primarily by economics. This is to be distinguished from the essence of the present invention, which is the creation of a palladium catalyst system which possesses a greatly improved efficiency, per se. The starting materials themselves, the halobenzene compound and salicylic acid alkyl ester, are employed in approximately stoichiometric amounts, i.e., on a mole per mole basis, although the reaction kinetics, particularly as these are affected by the palladium catalyst system, will dictate the preferred ratio of starting materials. It has also been found desirable to maintain this desired ratio of starting materials throughout the course of the reaction by means of continuous feed of the salicylic acid alkyl ester starting material.

Another important component of the catalyst portion of the palladium catalyst system of the present invention is a reaction promoting acid. This acid should be an organic acid rather than a mineral acid, and suitable acids are, for example, formic acid; acetic acid; propionic acid; butyric acid; mono-, di-, and trichloroacetic acid; mono-, di-, and trifluoroacetic acid; perchloric acid; and methanesulfonic acid. The reaction promoting acid is employed in amounts of from 10 to 100 parts per part on a molar basis of the palladium catalyst.

With regard to improved turnover numbers for the catalyst system, when the turnover number is one and the reaction is stoichiometric rather than catalytic, as in some prior art methods, the palladium will usually be found to have precipitated out as palladium black, and thus no longer able to function as a catalyst. By contrast, the novel improved method of the present invention affords regeneration of the catalyst many times before eventual inactivation, thus giving a very high turnover number.

Thus, in accordance with the procedures of the method of the present invention, the catalyst regeneration portion of the palladium catalyst system comprises (a) a solubilizing agent comprising ethylene carbonate, propylene carbonate, or sulfolane, preferably ethylene carbonate; and (b) an oxidant comprising a phosphomolybdenovanadic acid.

Phosphomolybdenovanadic acids are heteropolyacids of the formula $H_{3+n}[PMo_{12-n}V_nO_{40}]$, where n is 1 to 4. A preferred acid of this type is that where n is 2, with the following formula: $H_5PMo_{10}V_2O_{40}$. For details concerning preparation of compounds of this type, see Kokorin, Zh. Obshch. Khim., 24, 966 (1954). Acids of this type have been employed heretofore to regenerate palladium complexes. See Matveev et al., Kinetika i Kataliz, Vol. 18, No. 2, pp. 380–386 (1977) and Rudenkov et al., cited above. However, there is no teaching in the cited prior art of the unique catalyst regeneration system utilized in the method of the present invention which affords a significantly improved number of turnovers.

The amount of phosphomolybdenovanadic acid employed will be from 0.1 to 3.0 parts per part on a mole basis of palladium catalyst utilized, although amounts in excess of 3.0 moles, up to 8.0 or more moles may be used without adversely affecting regeneration of the palladium catalyst. Preferably the phosphomolybdenavanadic acid will be employed on a mole per mole basis.

The remaining component of the catalyst regeneration portion of the palladium catalyst system utilized in the method of the present invention, the solubilizing agent, preferably ethylene carbonate, is employed in amounts of at least 20 parts per part on a molar basis of palladium catalyst utilized. However, the solubilizing agent functions essentially as a solvent and, consequently, amounts considerably in excess of 20 parts per part of palladium catalyst may be employed without detriment.

The first step of the novel improved method of the present invention is carried out at a temperature of from 80° to 150° C., preferably from 90° to 120° C. The reaction is carried out in an oxygen atmosphere at a pressure ranging from atmospheric pressure to 750 p.s.i.g.

In the second step of the method of the present invention, the alkyl ester of the 5-(halophenyl)salicylic acid compound obtained in the first step of the method is hydrolyzed to give the corresponding salicylic acid. This second step employs hydrolysis techniques known in the art. Thus, for example, the alkyl ester may be first refluxed with aqueous sodium hydroxide, cooled, acidified, extracted with toluene, and finally crystallized to give the final acid product.

Following is a list of the components and amounts utilized in a typical first step reaction for the method of the present invention:

| Compound | Amount |
|---|---|
| M-Difluorobenzene | 510 mmole |
| Methyl salicylate | 389 mmole |
| Palladium acetate | 1 mmole |
| Sodium chloride | 2 mmole |
| Phosphomolybdenovanadic acid | 1 mmole |
| Ethylene carbonate | 227 mmole |
| Acetic acid | 33 mmole |

In summary, the novel improved method of the present invention may be described as a method of preparing compounds of Formula I. comprising the steps of:

(a) combining, in the presence of a palladium catalyst system, and at a temperature of from 80° to 150° C. and a pressure of from atmospheric to 750 p.s.i.g., a halobenzene compound of the formula:

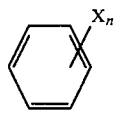
(IV)

where X is chloro or fluoro and n is 1 or 2, with a salicylic acid ester of the formula:

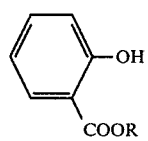
(III.)

where R is $C_{1-4}$ alkyl;
wherein said palladium catalyst system comprises:

A. a catalyst portion comprising:

(1) from 0.1 to 4.0 parts of palladium for every 500 parts, on a molar basis, of said halobenzene compound; together with (2) $C_{1-2}COO^-$ ligands, and halo ligands selected from the group consisting of bromo, chloro, and fluoro, such that the molar weight percent, based on total ligand molar weight, of the $C_{1-2}COO^-$ ligands is from 30 to 60%; wherein the $C_{1-2}COO^-$ ligands are provided as palladium or alkali metal, acetate or propionate, and said halo ligands are provided as the appropriate halo salt of palladium, lithium, sodium, or tetra (alkyl) ammonium;

wherein the ratio of the total molar weight amount of the ligands to the molar weight amount of palladium utilized, is from 4:1 to 10:1; and (3) from 10 to 100 parts of a reaction promoting acid, per part, on a molar basis, of palladium catalyst; and B. a catalyst regeneration portion comprising:

(1) from 0.1 to 8.0 parts of phosphomolybdenovanadic acid per part, on a molar basis, of palladium catalyst; and (2) at least 20 parts of a solubilizing agent selected from the group consisting of ethylene carbonate, propylene carbonate, and sulfolane, per part, on a molar basis, of palladium catalyst;

to give a compound of the formula:

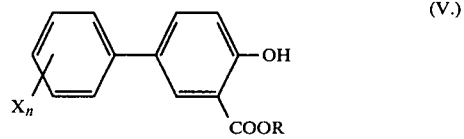
(V.)

(b) hydrolyzing the product of Step (a) to give the compound of Formula I.

The following examples will serve to illustrate the manner in which the method of the present invention may be carried out.

EXAMPLE 1

Preparation of 5-(2,4-difluorophenyl)salicylic acid

A. Methyl 5-(2,4-difluorophenyl)salicylate

A glass lined autoclave is charged with 224.5 mg. (1 mmole) of palladium acetate, 292.3 mg. (5.0 mmole) of sodium chloride, 131.3 mg. (1.6 mmole) of sodium acetate, 3.5 g. of $H_5PMo_{10}V_2O_{40}$ (2.0 mmole), 10 g. of ethylene carbonate, 5.0 ml. of acetic acid, 60 ml. (466 mmole) of methyl salicylate and 50 ml. (510 mmole) of m-difluorobenzene. The mixture is stirred for 48 hours at 90° C. and 200 p.s.i. oxygen pressure. The solution is cooled to 25° C. and excess m-difluorobenzene is removed by distillation. Fifty ml. of water and 150 ml. of toluene are then added to the residue. The pH is adjusted to 7-8 with aqueous sodium hydroxide (80 mmoles). The layers are separated and the aqueous solution is extracted with 150 ml. of toluene. The toluene and then the methyl salicylate (192 mmole) are removed by distillation. The residue is taken up in 60 ml. of hot n-propanol, and upon cooling methyl 5-(2,4-difluorophenyl)salicylate crystallizes out. Filtration yields 7.92 g. (30 mmole) of product, a 3000% yield based on palladium acetate.

B. 5-(2,4-difluorophenyl)salicylic acid

The product of Step A. above is suspended in 80 ml. of aqueous sodium hydroxide (5%) and refluxed for 30 minutes. The mixture is acidified with aqueous hydrochloric acid and extracted three times with 150 ml. of toluene. The combined toluene extracts are concentrated and the 5-(2,4-difluorophenyl)salicylic acid is crystallized out. Filtration yields 29.4 mmole of final product, a 98% yield.

EXAMPLES 2–13

The procedures of Step A. of Example 1 above were followed in twelve different runs, varying the amounts of reactants and catalyst components, as well as the time, temperature, and pressure parameters of the reaction. The results obtained with those different runs are illustrated in the following table of values.

| Example No. | Pd[a] (OAc)$_2$ (mmole) | Na[a] OAc (mmole) | NaCl[a] (mmole) | PMV[a] (mmole) | EC[a] (g.) | AcOH[a] (ml.) | DFB[a] (mmole) | MS[a] (mmole) | Temp. (°C.) | Oxygen Pressure (p.s.i.g.) | Time (Hr.) | Moles Prod.[d] Moles Palladium |
|---|---|---|---|---|---|---|---|---|---|---|---|---|
| 1 | 1.0 | 1.7 | 6.8 | 1.9 | 10.0 | 5.0 | 306 | 466 | 90 | 200 | 72 | 19.2 |
| 2 | 1.0 | 1.6 | 5.0 | 2.0 | 10.0 | 5.0 | 510 | 466 | 90 | 200 | 42 | 30.1 |
| 3 | 0.1 | — | 0.2 | 0.1 | 2.0 | 0.2 | 51 | 38.9 | 100 | 200 | 18 | 24.3 |
| 4 | 0.1 | — | 0.2 | 0.1 | 2.0 | 0.2 | 51 | 38.9 | 100 | 600 | 17 | 30.8 |
| 5 | 0.1 | — | 0.2 | 0.1 | 2.0 | 0.2 | 51 | 38.9 | 100 | 80 | 19 | 22.5 |
| 6 | 0.1 | — | 0.2[b] | 0.1 | 2.0 | 0.2 | 51 | 38.9 | 100 | 600 | 17.3 | 13.5 |
| 7 | 1.0 | 1.6 | 5.0 | 1.9 | 10.0 | 5.0 | 510 | 466 | 90 | 200 | 70.5 | 32.6 |
| 8 | 0.1 | — | 0.2 | 0.1 | 2.0 | 0.2[c] | 51 | 38.9 | 100 | 600 | 18 | 24.9 |
| 9 | 0.1 | — | 0.2 | 0.1 | 2.0 | 0.2 | 51 | 38.9 | 100 | 600 | 18 | 23.4 |
| 10 | 0.1 | — | 0.2 | 0.1 | 5.0 | 0.2 | 51 | 38.9 | 100 | 600 | 65 | 27.2 |
| 11 | 0.1 | — | 0.2 | 0.1 | 8.0 | 0.2 | 51 | 38.9 | 100 | 600 | 62 | 18.4 |
| 12 | 1.0 | 1.6 | 5.0 | 1.9 | 10.0 | 5.0 | 510 | 466 | 110 | 200 | 24 | 19.9 |

[a]The abbreviations employed have the following meanings: Pd (OAc)$_2$ = Palladium Acetate, Na OAc = Sodium Acetate, NaCl = Sodium Chloride, PMV = phosphomolybdenovanadic, EC = Ethylene Carbonate, AcOH = Acetic Acid, DFB = M-Difluoro Benzene, and MS = Methyl Salicylate
[b]Tetraethylammonium fluoride was substituted for sodium chloride.
[c]Trifluoroacetic acid was substituted for acetic acid.
[d]Product = Methyl 5-(2,4-difluorophenyl)salicylate

What is claimed is:

1. A method of preparing compounds of the formula:

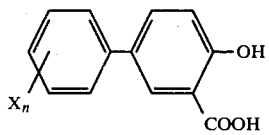

(I.)

where
n is 1 or 2; and
X is chloro or fluoro comprising the steps of:
(a) combining, in the presence of a palladium catalyst system, and at a temperature of from 80° to 150° C. and a pressure of from atmospheric to 750 p.s.i.g., a halobenzene compound of the formula:

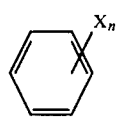

where X is chloro or fluoro and n is 1 or 2, with a salicylic acid ester of the formula:

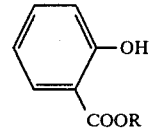

where R is $C_{1-4}$ alkyl;
wherein said palladium catalyst system comprises:
A. a catalyst portion comprising:
(1) palladium together with
(2) $C_{1-2}COO^-$ ligands and halo ligands selected from the group consisting of bromo, chloro, and fluoro, such that the molar weight percent, based on total ligand molar weight, of the $C_{1-2}COO^-$ ligands is from 30 to 60%; wherein the $C_{1-2}COO^-$ ligands are provided as palladium or alkali metal, acetate or propionate, and said halo ligands are provided as the appropriate halo salt of palladium, lithium, sodium, or tetra (alkyl) ammonium;
wherein the ratio of the total molor weight amount of the ligands to the molar weight amount of palladium utilized, is from 4:1 to 10:1; and
(3) from 10 to 100 parts of a reaction promoting acid, per part, on a molar basis, of palladium catalyst; and
B. a catalyst regeneration portion comprising:
(1) from 0.1 to 8.0 parts of phosphomolybdenovanadic acid per part, on a molar basis, of palladium catalyst; and
(2) at least 20 parts of a solubilizing agent selected from the group consisting of ethylene carbonate, propylene carbonate, and sulfolane, per part, on a molar basis, of palladium catalyst;
to give a compound of the formula:

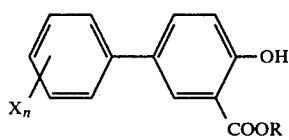

(b) hydrolyzing the product of Step (a) to give the compound of Formula I.

2. The method of claim 1 wherein the temperature is from 90° to 120° C.

3. The method of claim 1 wherein the starting materials are m-difluorobenzene and methyl salicylate.

4. The method of claim 1 wherein the catalyst portion comprises palladium acetate, sodium chloride, and acetic acid; and the catalyst regeneration portion comprises phosphomolybdenovanadic acid and ethylene carbonate.

5. The method of claim 1 wherein the amount of palladium catalyst employed is from 0.1 to 4.0 parts per 500 parts, on a molar basis, of the halobenzene compound.

6. The method of claim 1 wherein the molar weight ratio of the ligands to palladium is 4:1.

7. The method of claim 1 wherein the reaction promoting acid is selected from the group consisting of formic acid; acetic acid; propionic acid; butyric acid; mono-, di-, and trichloroacetic acid; mono-, di-, and trifluoroacetic acid; perchloric acid; and methanesulfonic acid.

* * * * *

UNITED STATES PATENT OFFICE
CERTIFICATE OF CORRECTION

Patent No. 4,237,315                    Dated December 2, 1980

Inventor(s) Ulf H. Dolling

It is certified that error appears in the above-identified patent and that said Letters Patent are hereby corrected as shown below:

Col. 7, line 58, the sentence which reads "and a pressure of from atmospheric to 750 p.s.i.g." should read -- and under an oxygen atmosphere at a pressure of from atmospheric to 750 p.s.i.g. --.

Col. 8, line 44, the word "molor" should be -- molar --.

Signed and Sealed this

Eleventh Day of August 1981

[SEAL]

Attest:

GERALD J. MOSSINGHOFF

Attesting Officer            Commissioner of Patents and Trademarks